United States Patent [19]
Harvey

[11] Patent Number: 6,165,987
[45] Date of Patent: Dec. 26, 2000

[54] ANTHELMINTIC FORMULATIONS

[76] Inventor: Colin Manson Harvey, 55 Beach Road, Castor Bay, Auckland, New Zealand

[21] Appl. No.: 09/214,543
[22] PCT Filed: Jul. 25, 1997
[86] PCT No.: PCT/NZ97/00096
  § 371 Date: Jan. 6, 1999
  § 102(e) Date: Jan. 6, 1999
[87] PCT Pub. No.: WO98/06407
  PCT Pub. Date: Feb. 19, 1998

[30] Foreign Application Priority Data

Jul. 30, 1996 [NZ] New Zealand ............................ 299094
Sep. 13, 1996 [NZ] New Zealand ............................ 299387

[51] Int. Cl.[7] ......................... A61K 31/70; A61K 31/50; A61K 31/45
[52] U.S. Cl. ......................... 514/30; 514/248; 514/249; 514/250; 514/724
[58] Field of Search .................. 514/250, 30, 248, 514/249, 724

[56] References Cited

U.S. PATENT DOCUMENTS 4,113,867  9/1978  Seubert et al. ......................... 424/450
5,089,480  2/1992  Gibson et al. ........................... 514/30
5,824,653  10/1998 Beuvry et al. .......................... 514/30

FOREIGN PATENT DOCUMENTS 2252730  8/1992  United Kingdom .

OTHER PUBLICATIONS

International Search Report, International Application No. PCT/NZ97/00096.

Primary Examiner—Kevin E. Weddington
Attorney, Agent, or Firm—Volpe and Koenig, P.C.

[57] ABSTRACT

A veterinary composition containing an effective amount of praziquantel, an effective amount of at least one macrolide anthelmintic selected from the group comprising the avermectins and the milbemycins, and a suitable organic solvent selected from the group consisting of glycerol formal, ethyl lactate, benzyl alcohol and N-methyl-2-pyrrolidone and the like wherein the composition is suitable for administration to warm-blooded non-human animals. The composition may be a solution or a paste and may be administered to the recipient animal by injection, drench or as an oral paste. A method of treating endo- and ectoparasites in non-human animals is also claimed.

22 Claims, No Drawings

ANTHELMINTIC FORMULATIONS

This application is a 371 of PCT/NZ97/00096 filed Jul. 25, 1997.

TECHNICAL FIELD OF THE INVENTION

This invention relates to solutions containing the anthelmintic, praziquantel.

BACKGROUND

In recent years the new anthelmintic compounds of the macrolide group such as avermectins and milbemycins have been drugs of choice for the treatment of internal parasites of sheep, cattle and other farm animals. These compounds offer not only the control of many internal parasites but also external parasites and therefore have become known as endecticides. Their popularity has increased because of their dual activity and because of increasing resistance to other traditional anthelmintics like levamisole and the benzimidazoles.

However, unlike the benzimidazoles, the macrolide anthelmintics need to be administered as solutions to be bio-available as in their solid form they are poorly absorbed by the animal. It has therefore been the practice to formulate these compounds by dissolving them in solvents before administration.

Some types of parasites, particularly trematodes, that are not controlled by the macrolide endecticides. Important trematodes in sheep for example are Liver Fluke (*Fasciola hepatica*) and Tapeworm (Monezia spp.).

Previous methods of incorporating anthelmintics that have activity against trematodes have relied on suspending a compound like praziquantel that controls Monezia spp. in an anthelmintic solution. It is more desirable to have dual formulations as solutions as this allows wider application as injectables or drenches.

OBJECT

It is an object of this invention to provide a composition containing an effective amount of praziquantel and at least one of the active anthelmintics of the macrolide group or at least one that provides the public with a useful choice.

STATEMENT OF INVENTION

In one aspect the invention comprises veterinary composition containing:
a) an effective amount of praziquantel;
b) an effective amount at least one macrolide anthelmintic selected from the group comprising the avermectins and the milbemycins; and
c) a suitable organic solvent capable of dissolving a) and b);

wherein the composition is suitable for administration to warm-blooded non-human animals.

Preferably the solvent is an ester or ester-like compound. Certain esters and similar compounds have the benefit of dissolving both praziquantel and the avermectins and milbemycins without being toxic to animals.

More preferably the solvent is selected from the group consisting of glycerol formal, ethyl lactate, benzyl alcohol, N-methyl-2-pyrrolidone and the like.

Preferably the composition is further dissolved in a carrier selected from the group consisting of monoproylene glycol, oil, water and the like.

Preferably the composition is a solution.

Preferably the macrolide anthelmintic is present in the composition in the range from 0.1–2% w/v and the praziquantel is preferably present in the composition in the range from 1–10% w/v.

Alternatively the composition is a paste containing:
(a) a solution of an effective amount of praziquantel, an effective amount at least one macrolide anthelmintic selected from the group comprising the avermectins and the milbemycins, and a suitable organic solvent; and
(b) a thickener.

Preferably the thickener is a solid carrier onto which the solution is absorbed and is selected from the group comprising oat meal flour, methancel, and xanthan gum.

Preferably the macrolide anthelmintic is present in the paste in the range from 0.1–2% w/v and the praziquantel is preferably present in the composition in the range from 1–10% w/v.

In another aspect the invention provides a method for the treatment of endo- and ectoparasites in a non-human animal by administering to an animal a composition as described above at the rate of 1 ml/5–20 kg of bodyweight.

Preferably the animal is treated every 6–8 weeks or more often as required.

Preferably the composition is administered to the animal as a drench, by injection or as an oral paste.

PREFERRED EMBODIMENT

These and other aspects of this invention, which should be considered in all its novel aspects will be apparent from the following examples.

EXAMPLE 1

Formulation Type: Drench
Intended Recipient Animals: Sheep, Cattle, Goats

| Ingredient | % w/v |
|---|---|
| Ivermectin | 0.2 |
| Praziquantel | 4.0 |
| Tween 80 | 10.0 |
| Glycerol Formal | 10.0 |
| Benzyl Alcohol | 4.0 |
| Propyl Gallate | 0.009 |
| Monopropylene Glycol | 40.0 |
| Deionised water | 20.0 |
| Disodium EDTA | 0.009 |
| Sodium dihydrogen phosphate | 0.5 |
| Disodium hydrogen phosphate | 0.5 |
| Mineral Premix | 10.0 |
| Selenium Chelate | 0.305 |
| Monopropylene Glycol | To volume |
| | 100.0 mL |

The mineral premix is a chelated mineral mixture of Copper, Cobalt and Zinc.

Example 1 is manufactured as follows:
1. To a clean dry mixing vessel add the benyl alcohol and with stirring add the ivermectin. Stir until completely dissolved.
2. Add the Tween 80 and glycerol formal and stir until completely dispersed.
3. Add the praziquantel while stirring and warm the solution to 50–60° C. Continue stirring until fully dissolved.

4. Add the propyl gallate and stir until dissolved.
5. Add the monopropylene glycol and stir to mix.
6. To a separate mixing vessel add the deionised water and with stirring add the disodium EDTA, sodium dihydrogen phosphate and disodium hydrogen phosphate in order ensuring each is fully dissolved before the next is added.
7. Add the sodium chelate and stir until fully dissolved.
8. Add the mineral premix and stir well to mix.
9. With stirring add the water phase to the solvent phase and stir until fully mixed (should be a clear dark blue solution).
10. Make up volume with monopropylene glycol and stir well to mix.
11. Package the product in appropriate packaging.

EXAMPLE 2a

Formulation Type: Drench
Intended Recipient Animal: Sheep, Cattle, Goats

| Ingredient | % w/v |
| --- | --- |
| Ivermectin | 0.1 |
| Praziquantel | 1.88 |
| Tween 80 | 10.0 |
| Glycerol Formal | 10.0 |
| Benzyl Alcohol | 4.0 |
| Propyl Gallate | 0.009 |
| Monopropylene Glycol | 40.0 |
| Deionised water | 20.0 |
| Disodium EDTA | 0.009 |
| Sodium dihydrogen phosphate | 0.5 |
| Disodium hydrogen phosphate | 0.5 |
| Mineral Premix | 10.0 |
| Selenium Chelate | 0.305 |
| Monopropylene Glycol | To volume |
| | 100.0 mL |

The mineral premix is a chelated mineral mixture of Copper, Cobalt and Zinc.

EXAMPLE 2b

Formulation Type: Drench
Intended Recipient Animal: Sheep, Cattle, Goats

| Ingredient | % w/v |
| --- | --- |
| Abamectin | 0.1 |
| Praziquantel | 1.88 |
| Tween 80 | 10.0 |
| Glycerol Formal | 10.0 |
| Benzyl Alcohol | 4.0 |
| Propyl Gallate | 0.009 |
| Monopropylene Glycol | 40.0 |
| Deionised water | 20.0 |
| Disodium EDTA | 0.009 |
| Sodium dihydrogen phosphate | 0.5 |
| Disodium hydrogen phosphate | 0.5 |
| Mineral Premix | 10.0 |
| Selenium Chelate | 0.305 |
| Monopropylene Glycol | To volume |
| | 100.0 mL |

The mineral premix is a chelated mineral mixture of Copper, Cobalt and Zinc.

Examples 2a and 2b are manufactured as follows:
1. To a clean dry mixing vessel add the benzyl alcohol and with stirring add the ivermectin or abamectin. Stir until completely dissolved.
2. Add the Tween 80 and glycerol formal and stir until completely dispersed.
3. Add the praziquantel while stirring and warm the solution to 50–60° C. Continue stirring until fully dissolved.
4. Add the propyl gallate and stir until dissolved.
5. Add the monopropylene glycol and stir to mix.
6. To a separate mixing vessel add the deionised water and with stirring add the disodium EDTA, sodium dihydrogen phosphate and disodium hydrogen phosphate in order ensuring each is fully dissolved before the next is added.
7. Add the sodium chelate and stir until fully dissolved.
8. Add the mineral premix and stir well to mix.
9. With stirring add the water phase to the solvent phase and stir until fully mixed (should be a clear dark blue solution).
10. Make up volume with monopropylene glycol and stir well to mix.
11. Package the product in appropriate packaging.

EXAMPLE 3

Formulation Type: Drench
Intended Recipient Animals: Sheep, Cattle, Goats

| Ingredient | % w/v |
| --- | --- |
| Abamectin | 0.113 |
| Praziquantel | 1.88 |
| Selenium ($Na_2Se$) | 0.305 |
| Mineral Premix | 10.00 |
| Polysorbate 80 BP | 5.00 |
| Benzyl Alcohol BP | 2.00 |
| Ethyl Lactate | 10.00 |
| Potassium Sorbate | 0.18 |
| Formalin | 0.20 |
| Purified water BP | 20.00 |
| Sodium Phosphate BP | 0.10 |
| Sodium Acid Phosphate | 0.90 |
| Propylene Glycol BP | to volume |
| | 100.0 mL |

The mineral premix is a chelated mineral mixture of Copper, Cobalt and Zinc.

Example 3 is manufactured as follows:
1. To a clean dry mixing vessel add the ethyl lactate, benzyl alcohol and Polysorbate 80.
2. While stirring add the abamectin and praziquantel and stir until dissolved.
3. To a separate mixing vessel add the water and dissolve in the potassium sorbate.
4. Add the sodium phosphate and sodium acid phosphate and stir until fully dissolved.
5. Add the selenium and mineral premix and stir to dissolve.
6. Add the water mix to the abamectin/praziquantel mix and stir well to mix.
7. Add the formalin and stir well.
8. Make up to volume with the propylene glycol.
9. Package the product in suitable container.

Examples 1, 2a, 2b and 3 produce stable solutions that are aqueous based. They may be administered at a rate of 1 mL/5–20 kg of bodyweight of the animal every 6–8 weeks or as required.

EXAMPLE 4

Formulation Type: Oral Paste
Intended Recipient Animals: Horses and Companion Animals

| Ingredient | % w/v |
| --- | --- |
| Abamectin | 0.400 |
| Praziquantel | 5.000 |
| DiEthylene Glycol Palmito Stearate (DEGPS) | 8.000 |
| Oat Meal Flour | 30.00 |
| Sodium Metabisulfite | 0.100 |
| Sorbitol Solution (non-crystallising) | 12.00 |
| Glycerol Formal | 6.000 |
| PolyEthylene Glycol 400 | 6.000 |
| Methyl Hydroxybenzoate | 0.050 |
| Propyl Hydroxybenzoate | 0.005 |
| Benzyl Alcohol | 1.000 |
| Purified Water | To volume |
| | 100.0 mL |

Example 4 is manufactured as follows:

1. In a separate container, heat purified water to 80–85°. Maintain at this temperature.
2. While mixing, add and dissolve methyl hydroxybenzoate and propyl hydroxybenzoate. Continue mixing until all has dissolved.
3. While mixing, add sorbitol solution. Maintain the temperature at 70° C.
4. In a separate container add glycerol formal, polyethylene glycol 400 and benzyl alcohol. Start mixing while warming to 35–40° C.
5. While mixing, add abamectin. Continue mixing until all has dissolved. Maintain temperature at 35–40° C.
6. In the ointment tank add half the oat meal flour and the praziquantel and then start mixing. Continue mixing for 5–10 minutes then add the rest of the oat meal flour and continue mixing until a homogenous blended powder is formed.
7. While mixing the powders add the solution from step 5 in a thin stream. When all is added continue mixing until a homogenous mass is formed.
8. Melt DiEthylene Glycol Palmito Stearate (DEGPS) in a separate container. While mixing the solution from step 3, add the melted wax and continue mixing to form an homogenous emulsion. Stop heating and mix to cool to 40–45° C.
9. Add and dissolve sodium metabisulfite in the emulsion.
10. While mixing the mass from step 7, add gradually and in a thin stream the emulsion from step 9. Emulsion when added should be at 40–45° C.
11. When all is added continue mixing for 10–15 minutes descaping the walls occassionally.
12. Complete the batch to volume with purified water while mixing. Continue mixing for 30 minutes. Stop when the batch temperature is not higher than 30° C. Check the specific gravity (1.05–1.09).
13. Homogenise the batch. When completed the batch is in the form of a smooth paste, free from lumps or grittiness, beige in colour and has a pleasant characteristic odour.
14. Package in paste syringes.

In example 4 oat meal flour is used as a solid carrier. Other examples of solid carriers that could be used are methancel or xanthan gum.

Example 4 produces a spreadable, viscous paste which may be administered to an animal as an oral paste at the rate of 1 mL/5–20 kg of bodyweight of the animal every 6–8 weeks or as required. The formulation is aqueous based.

EXAMPLE 5

Formulation Type: Drench
Intended Recipient Animals: All Farm Animals

| Ingredient | % w/v |
| --- | --- |
| Abamectin | 0.100 |
| Praziquantel | 1.880 |
| Benzyl Alcohol | 10.00 |
| Soyabean oil | To volume |
| | 100.0 mL |

Example 5 is preferably manufactured as follows:

1. To a clean dry mixing vessel add the Benzyl Alcohol, and while stirring add the Abamectin and Praziquantel. Continue to stir until completely dissolved.
2. Make up to volume with the Soyabean Oil and stir well to mix.
3. Package the product in suitable packaging.

Example 5 produces a solution that is oil based. It may be administered at a rate of 1 mL/5–20kg of bodyweight of the animal every 6–8 weeks or as required.

EXAMPLE 6

Formulation Type: Injectable
Intended Recipient Animals: All Farm Animals

| Ingredient | % w/v |
| --- | --- |
| Abamectin | 1.22 |
| Praziquantel | 15.0 |
| Glycerol Formal | 60.0 |
| Monopropylene Glycol | To volume |
| | 100.0 mL |

Example 6 is manufactured as follows:

1. To a clean dry mixing vessel add the glycerol formal and while stirring add the abamectin and praziquantel. Continue to stir until dissolved.
2. Make up to volume with monopropylene glycol and stir well.
3. Sterilise product by suitable filtration and pack under sterile conditions into suitable injection bottles.

Example 6 produces a solution that is suitable for injection. It may be administered at a rate of 1 mL/5–20kg of bodyweight of the animal every 6–8 weeks or as required.

EXAMPLE 7

Formulation Type: Injection or Drench
Intended Recipient Animals: All Farm Animals

| Ingredient | % w/v |
| --- | --- |
| Abamectin | 1.22 |
| Praziquantel | 15.0 |
| N-Methyl-2-Pyrolidone | 60.0 |
| Sesame Oil | To volume |
| | 100.0 mL |

Example 7 is manufactured as follows:

1. To a clean dry mixing vessel add the glycerol formal and while stirring add the abamectin and praziquantel. Continue to stir until dissolved.
2. Make up to volume with sesame oil and stir well.
3. Package product under sterile conditions into suitable injection bottles or in suitable containers for a drench formulation.

Example 7 produces an oil based solution that is suitable for administration as an injection or a drench. It may be administered at a rate of 1 mL/5–20 kg of bodyweight of the animal every 6–8 weeks or as required.

The compositions of the invention are stable and have been shown to be non-toxic to animals.

STABILITY

EXAMPLE 3

Stability Trial

A solution according to example 3 was prepared and tested for stability. The solution was stored at ambient temperature in a black high density polyethylene container with a black high density polyethylene cap.

A variety of tests were performed on the composition initially, and then at 3 months, 6 months and one year. The results are set out in Table 1.

There was no loss of stability of the composition over the trial period.

Copper, cobalt and zinc are included in the mineral premix of example 3. Selenium is added separately to the composition.

EXAMPLE 4

Stability Trial

A spreadable paste according to example 4 was prepared and tested for stability at 30° C. and at 40° C.

The paste was stored in a plastic syringe inside a carton.

The amount of the active ingredients was measured initially, and then at one month, three months and six months. The results are set out below in Table 2 and Table 3.

TABLE 2

Stability of Example 4 at 30° C.

| | Initial | 1 Month | 3 Months | 6 Months |
| --- | --- | --- | --- | --- |
| Abamectin (g/kg) | 3.5 | 3.7 | 3.6 | 3.6 |
| Total Avermectin (g/kg) | 3.7 | 3.9 | 3.8 | 3.8 |
| Praziquantel (g/kg) | 50 | 50 | 46 | 48 |

[Differences in Abamectin and Total Avermectin concentrations over the trial period was within the margin of error for the trial]

TABLE 3

Stability of Example 4 at 40° C.

| | Initial | 1 Month | 3 Months | 6 Months |
| --- | --- | --- | --- | --- |
| Abamectin (g/kg) | 3.5 | 3.4 | 3.1 | 3.4 |
| Total Avermectin (g/kg) | 3.7 | 3.6 | 3.3 | 3.7 |
| Praziquantel (g/kg) | 50 | 48 | 48 | 49 |

[Differences in Abamectin and Total Avermectin concentrations over the trial period was within the margin of error for the trial]

TABLE 1

Stability of Example 3

| Test | Initial | 3 Months | 6 Months | 1 Year |
| --- | --- | --- | --- | --- |
| Appearance | Clear, blue liquid | Clear, blue liquid | Clear, blue liquid | Clear, blue liquid |
| Appearance after inversion | Okay | Okay | Okay | Okay |
| Density at 20° C. (g/mL) | 1.062 | 1.063 | 1.065 | 1.067 |
| Viscosity at 20° C. Ford #4 Cup (Seconds) | 14 | 14 | 14 | 14 |
| Bottle condition | Okay | Okay | Okay | Okay |
| pH | 6.7 | 6.4 | 5.8 | 5.8 |
| Praziquantel (g/L) | 18.9 | 17.9 | 18.9:18.9* | 18.9 |
| Abamectin (g/L) | 1.09 | 1.00 | 1.03:1.04* | 0.95 |
| MINERAL PREMIX | | | | |
| - Copper (g/L) | 2.12 | 2.19 | 2.24 | 2.23 |
| - Cobalt (g/L) | 0.24 | 0.21 | 0.20:0.21* | 0.20:0.20 |
| - Zinc (g/L) | 0.61 | 0.60 | 0.58:0.56* | 0.63 |
| Selenium (g/L) | 0.45 | 0.49 | 0.48 | 0.50:0.50 |

[*Repeat assays carried out where first assay result was in doubt]

EFFICACY

The efficacy of example 3 (Speedwell P Mineral Drench for Sheep) and example 3 without praziquantel (Speedwell Mineral Drench for Sheep) in the control and treatment of naturally occurring infection with common pathogenic nematodes and cestodes was assessed against the commercially available product Ivomec Liquid for Sheep and Goats (Merck Sharp & Dohme).

The study and interpretation of the raw data was undertaken in accordance with the World Association for the Advancement of Veterinary Parasitology (WAAVP) guidelines.

Abamectin stimulates the release of a neurotransmitter, gamma aminobuteryic acid (GABA) from the nerve endings and enhances its binding to GABA receptors at the nerve junctions. This action interrupts nerve impulses and leads to paralysis and death. It has no effect against cestodes, trematodes nor the mammalian peripheral nervous system.

Praziquantel inhibits cestode carbohydrate metabolism.

Allocation of Test Animals

Thirty-two clinically healthy Romney hoggets were used. The hoggets were selected on the basis of similar weight and overall body condition. No other medication was administered during the study period.

The hoggets were assigned randomly, on the basis of faecal egg count (FEC) and egg identification, to one of the following groups:
- Group 1: Control (untreated)
- Group 2: Positive Control (T1)
- Group 3: Test (T2)
- Group 4: Test (T3)

The hoggets were maintained together throughout the trial.

Treatment

Group 1: No treatment

Group 2: Hoggets were treated in accordance with Ivomec Batch 6639105 Exp. 01/95 label, ie 1 mL per 4 kg bodyweight (providing a dose of 200 $\mu$g Ivermectin per kg bodyweight)—T1

Group 3: Hoggets were treated with 1 mL Speedwell Mineral Drench Batch XIV-12 per 5 kg bodyweight (providing 200 $\mu$g Abamectin per kg bodyweight)—T2

Group 4: Hoggets were treated with 1 mL Speedwell P Mineral Drench Batch XIV-18 per 5 kg bodyweight (providing 200 $\mu$g Abamectin and 3.76 mg Praziquantel per kg bodyweight)—T3

Trial Activity and Design

Day-1 A group of 32 hoggets on the basis of similarity of bodyweight, overall body condition and health status were selected. A faecal egg count on all animals was carried out.

Day 0 On the basis of faecal egg count allocation was made randomly 8 animals to each group.

Day 1 Treatment of hoggets as follows:
- Group 1: No treatment
- Group 2: Ivomec treatment—T1
- Group 3: Speedwell Mineral Drench Treatment—T2
- Group 4: Speedwell P Mineral Drench Treatment—T3

Day 9 Faecal egg count on all hoggets.
Live weights taken.

Day 12 Hoggets slaughtered.
Removal of abomasum, and small and large intestines. Worms recovered, identified and counted.
Lungs were also examined for the presence of lungworm.

Parameters

Parameters for evaluation of Speedwell Mineral Drench and Speedwell P Mineral Drench efficacy and comparison with Ivomec treated and control groups were body weight, total egg count and total abomasal, intestine and lung worm count.

Assessment

Assessment was made by the clinical investigator. On the basis of satisfactory egg count on Day 9 total abomasal, intestine and lung counts proceeded.

Parasitology Analysis

Target parasite species were Haemonchus, Ostertagia, Trichostrongulus, Cooperia, Nematodirus, Oesophagostomum, Chabertis and *Monezia expansa*.

Total faecal egg count and necropsy procedures were performed by New Zealand Ministry of Agriculture and Fisheries Ruakura Animal Health Laboratory, Hamilton, New Zealand using approved and consistent methods and blind evaluation.

Results

The results of the trial are shown in tables 4–7 below.

Key for Tables 4–7:

Strong. Strongulus

Nema. Nematodirus

Haem. Haemonchus

Ostert. Ostertagia

Trich. Trichostrongulus

Coop. Cooperia

Scholex. Heads of *Monezia expansa*

Seg.mLs Segments (tape-like) of M expansa measured as millilitres

TABLE 4

| | | | \multicolumn{12}{c|}{Group 1 Control - No Treatment} |
| TAG | WGT. | DOSE | START | | POST DOSE | | \multicolumn{6}{c|}{12 DAY CRITICAL SLAUGHTER WORM COUNTS} | MONIEZA | |
| No. | kg. | ml. | Strong. | Nema. | Strong. | Nema. | Haem. | Ostert. | Trich. | Nema. | Trich. | Coop. | Scholex | Seg.mls. |
|---|---|---|---|---|---|---|---|---|---|---|---|---|---|---|
| 19 | 20 | — | 2100 | — | 1300 | — | — | 100 | 2800 | — | 23200 | 5200 | — | — |
| 36 | 22 | — | 3100 | — | 300 | — | — | 100 | 1900 | — | 6000 | 700 | — | — |
| 7 | 22 | — | 3100 | 50 | 2450 | — | — | 300 | 2200 | 200 | 14500 | 2800 | 4 | 30 |
| 35 | 24 | — | 2950 | — | 1650 | — | 100 | 700 | 13000 | — | 30000 | 4200 | 5 | — |
| 28 | 23 | — | 2300 | — | 1050 | — | — | 600 | 8800 | — | 20800 | 1600 | — | — |
| 2 | 21 | — | 2250 | — | 1300 | — | — | — | 2500 | 100 | 9200 | 2000 | 4 | 25 |
| 39 | 28 | — | 1700 | — | 800 | — | — | 200 | 10200 | — | 14400 | 2600 | — | — |
| 31 | 22 | — | 1550 | — | 1700 | — | — | 200 | 2800 | — | 17200 | 800 | — | 3 |
| MEAN | | | 2681 | 6.25 | 1318 | — | 12.5 | 275 | 5825 | 37.5 | 16912 | 2487 | 1.6 | 725 |

TABLE 5

Group 2 - IVOMEC (T1)

| TAG | WGT. | DOSE | START | | POST DOSE | | 12 DAY CRITICAL SLAUGHTER WORM COUNTS | | | | | | MONIEZIA | |
|---|---|---|---|---|---|---|---|---|---|---|---|---|---|---|
| No. | kg. | ml. | Strong. | Nema. | Strong. | Nema. | Haem. | Ostert. | Trich. | Nema. | Trich. | Coop. | Scholex | Seg.mls |
| 6 | 21 | 5.0 | 3350 | — | — | — | — | — | — | — | — | — | — | — |
| 18 | 18 | 4.5 | 3050 | — | — | — | — | — | — | — | — | — | — | — |
| 33 | 22 | 5.5 | 2850 | — | — | — | — | — | — | — | — | — | 1 | 1 |
| 40 | 24 | 6.0 | 2350 | 50 | — | — | — | — | — | — | — | — | — | — |
| 42 | 20 | 5.0 | 2100 | — | — | — | — | — | — | — | — | — | — | — |
| 17 | 26 | 6.5 | 2250 | — | — | — | — | — | — | — | — | — | — | — |
| 26 | 24 | 6.0 | 1150 | — | — | — | — | — | — | — | — | — | 3 | 1 |
| 25 | 22 | 5.5 | 600 | — | — | — | — | — | — | — | — | — | 8 | 32 |
| MEAN | | | 2212.5 | 6.25 | — | — | — | — | — | — | — | — | 1.5 | 4.25 |
| PERCENTAGE (%) | | | | | 99.9 | 99.9 | 99.9 | 99.9 | 99.9 | 99.9 | 99.9 | 99.9 | 6.25 | 41.3 |

TABLE 6

Group 3 - Speedwell Mineral Drench (T2)

| TAG | WGT. | DOSE | START | | POST DOSE | | 12 DAY CRITICAL SLAUGHTER WORM COUNTS | | | | | | MONIEZIA | |
|---|---|---|---|---|---|---|---|---|---|---|---|---|---|---|
| No. | kg. | ml. | Strong. | Nema. | Strong. | Nema. | Haem. | Ostert. | Trich. | Nema. | Trich. | Coop. | Scholex. | .Seg.mls |
| 41 | 18 | 3.5 | 6900 | 50 | — | — | — | — | — | — | — | — | 1 | 1 |
| 5 | 24 | 5.0 | 3300 | 50 | — | — | — | — | — | — | — | — | 3 | — |
| 3 | 22 | 4.5 | 3050 | — | — | — | — | — | — | — | — | — | 7 | 13 |
| 12 | 22 | 4.5 | 2900 | — | — | — | — | — | — | — | — | — | 3 | 30 |
| 15 | 24 | 5.0 | 2350 | — | — | — | — | — | — | — | — | — | 14 | 4 |
| 21 | 22 | 4.5 | 4550 | — | — | — | — | — | — | — | — | — | 5 | 2 |
| 38 | 22 | 4.5 | 1800 | — | — | — | — | — | — | — | — | — | 2 | 105 |
| 16 | 26 | 5.0 | 1550 | — | — | — | — | — | — | — | — | — | — | — |
| MEAN | | | 2446 | 12.5 | — | — | — | — | — | — | — | — | 4.37 | 19.37 |
| PERCENTAGE (%) | | | | | 99.9 | 99.9 | 99.9 | 99.9 | 99.9 | 99.9 | 99.9 | 99.9 | — | — |

TABLE 7

Group 4 - Speedwell P Mineral Drench (T3)

| TAG | WGT. | DOSE | START | | POST DOSE | | 12 DAY CRITICAL SLAUGHTER WORM COUNTS | | | | | | MONIEZIA | |
|---|---|---|---|---|---|---|---|---|---|---|---|---|---|---|
| No. | kg. | ml. | Strong. | Nema. | Strong. | Nema. | Haem. | Ostert. | Trich. | Nema. | Trich. | Coop. | Scholex | .Seg.mls |
| 4 | 22 | 4.5 | 5800 | — | — | — | — | — | — | — | — | — | — | — |
| 37 | 23 | 4.5 | 3000 | 50 | — | — | — | — | — | — | — | — | — | — |
| 34 | 22 | 4.5 | 2800 | — | — | — | — | — | — | — | — | — | — | — |
| 9 | 22 | 4.5 | 2750 | — | 1600 | — | — | — | — | — | — | — | — | — |
| 13 | 20 | 4.0 | 2050 | — | — | — | — | — | — | — | — | — | — | — |
| 23 | 27 | 5.5 | 1950 | — | — | — | — | — | — | — | — | — | — | — |
| 20 | 26 | 5.0 | 650 | — | — | — | — | — | — | — | — | — | — | — |
| 32 | 24 | 5.0 | 700 | — | — | — | — | — | — | — | — | — | — | — |
| MEAN | | | 2462.5 | 6.25 | 200 | — | — | — | — | — | — | — | — | — |
| PERCENTAGE (%) | | | | | 84.8 | 99.9 | 99.9 | 99.9 | 99.9 | 99.9 | 99.9 | 99.9 | 99.9 | 99.9 |

The data was analysed comparing treatment group means and in accordance with WAAVP guidelines.

The study compared the efficacies of Speedwell Mineral Drench Batch XIV-12 and Speedwell P Mineral Drench Batch XIV-18 based on pre- and post dosing FEC's and 12 day slaughter worm counts. When compared with Ivomec Batch 6639105 both products demonstrated 99.9% efficacy against nematodes when compared with the control group. Against Monezia expansa only Speedwell P Mineral Drench (containing praziquantel) demonstrated efficacy at 99.9%. Both Speedwell Mineral Drench and Ivomec were ineffective.

INDUSTRIAL APPLICATION

The veterinary compositions of the invention have been shown to be stable, non-toxic and effective in the treatment of endo- and ectoparasites in animals including but not limited to sheep, cattle, goats, and horses.

ADVANTAGES

It is advantageous to combine two or more anthelmintics with different activity in one composition to obtain a broad spectrum activity.

It is also advantageous to the user as only one treatment is needed against a number of parasites instead of two or more different treatments. This reduces the amount of time spent treating animals and therefore reduces stress to the animals themselves.

VARIATIONS

Although the above examples have concentrated on the use of praziquantel combined with abamectin or ivermectin, any other compound of the avermectin group could also be used.

In forming the compositions of the invention the active anthelmintic ingredients are dissolved in a solvent. In some instances it is preferred to thicken the resulting solution by absorbing it onto a solid carrier. These thickened solutions are also within the scope of the invention.

Finally, it will be appreciated that various other alterations and modifications may be made to the foregoing without departing from the scope of this invention.

What is claimed is:

1. A stable veterinary liquid anthelmintic composition suitable for administration to warm-blooded non-human animals at a dose of more than 2.0 mg of praziquantel per kilogram of body weight comprising:
   a) an effective amount of praziquantel;
   b) an effective amount of at least one macrolide anthelmintic selected from the group comprising the avermectins and the milbemycins; and
   c) a suitable organic solvent comprising an ester or ester like compound that dissolves praziquantel and the avermectin or milbemycin and is not toxic to animals.

2. A stable veterinary liquid anthelmintic composition as claimed in claim 1 wherein the organic solvent is selected from the group consisting of glycerol formal, ethyl lactate, benzyl alcohol and N-methyl-2-pyrrolidone and the like.

3. A stable veterinary liquid anthelmintic composition as claimed in claim 2 wherein the composition is further dissolved in a carrier selected from the group consisting of monopropylene glycol, oil, water and the like.

4. A stable veterinary liquid anthelmintic composition as claimed in claim 3 wherein the macrolide anthelmintic is ivermectin present in the range 0.1 to 0.2% w/v.

5. A stable veterinary liquid anthelmintic composition as claimed in claim 4 wherein the organic solvent includes both glycerol formal and benzyl alcohol.

6. A stable veterinary liquid anthelmintic composition as claimed in claim 5 wherein the carrier is monopropylene glycol.

7. A stable veterinary liquid anthelmintic composition as claimed in claim 6 wherein the composition also contains minerals.

8. A stable veterinary liquid anthelmintic composition as claimed in claim 3 wherein the macrolide anthelmintic is abamectin present in the range 0.1 to 2.0% w/v.

9. A stable veterinary liquid anthelmintic composition as claimed in claim 8 wherein the organic solvent includes both glycerol formal and benzyl alcohol.

10. A stable veterinary liquid anthelmintic composition as claimed in claim 9 wherein the carrier is monopropylene glycol.

11. A stable veterinary liquid anthelmintic composition as claimed in claim 10 wherein the composition also contains minerals.

12. A stable veterinary liquid anthelmintic composition as claimed in claim 3 wherein the macrolide anthelmintic is present in the range from 0.1–2% w/v and the praziquantel is present in the range from 1 to 15% w/v.

13. A method for the treatment of endo- and ectoparasites in a non-human animal by administrating to an animal at the rate of 1 mL/5–20 kg of body weight a stable liquid composition comprising:
   a) an effective amount of praziquantel;
   b) an effective amount of at least one macrolide anthelmintic selected from the group comprising the avermectins and the milbemycins; and
   c) a suitable organic solvent comprising an ester or ester like compound that dissolves praziquantel and the avermectin or milbemycin and is not toxic to animals;
      wherein the organic solvent is selected from the group consisting of glycerol formal, ethyl lactate, benzyl alcohol and N-methyl-2-pyrrolidone and the like; and
      wherein the composition is further dissolved in a carrier selected from the group consisting of monopropylene glycol, oil, water and the like.

14. A method for the treatment of endo- and ectoparasites in a non-human animal as claimed in claim 13 wherein the stable liquid composition is administered to animal as a drench or by injection.

15. A stable veterinary anthelmintic paste composition suitable for administration to warm-blooded non-human animals at a dose of more than 2.0 mg of praziquantel per kilogram of body weight, comprising:
   a) a solution of an effective amount of praziquantel; and
   b) an effective amount of at least one macrolide anthelmintic selected from the group comprising the avermectins and the milbemycins; and
   c) a solvent comprising a ester or ester like compound that dissolves praziquantel and the avermectin or milbemycin and is not toxic to animals; and
   d) a thickener.

16. A stable veterinary anthelmintic paste composition as claimed in claim 15 wherein the thickener is a solid carrier onto which the solution is absorbed and selected from the group comprising oat meal flour, methancel and xanthan gum.

17. A stable veterinary anthelmintic paste composition as claimed in claim 16 wherein the praziquantel is present in the range from 1–15% w/v.

18. A stable veterinary anthelmintic paste composition as claimed in claim 17 wherein the paste also includes a wax.

19. A stable veterinary anthelmintic paste composition as claimed in claim 18 wherein the wax is diethyl glycol palmite stearate.

20. A stable veterinary anthelmintic paste composition as claimed in claim 19 wherein the macrolide anthelmintic is abamectin present in the range 0.1 to 2.0% w/v.

21. A stable veterinary anthelmintic paste composition as claimed in claim 20, containing enough praziquantel that it is suitable for administration at a dose rate of from 2.5 mg to 10 mg of praziquantel per kilogram of body weight of the animal.

22. A method for the treatment of endo- and ectoparasites in a non-human animal by administering a paste formulation at the rate of 1 ml of paste for every 5 to 20 kg of body weight of the animal, the paste formulation comprising:
   a) a solution of an effective amount of praziquantel; and
   b) an effective amount of at least one macrolide anthelmintic selected from the group comprising the avermectins and the milbemycins; and
   c) a solvent comprising a ester or ester like compound that dissolves praziquantel and the avermectin or milbemycin and is not toxic to animals; and
   d) a thickener;

wherein the thickener is a solid carrier onto which the solution is absorbed and selected from the group comprising oat meal flour, methancel and xanthan gum;

wherein the praziquantel is present in the range from 1–15% w/v;

wherein the paste also includes a wax;

wherein the wax is diethyl glycol palmite stearate; and wherein the macrolide anthelmintic is abamectin present in the range 0.1 to 2.0% w/v.

* * * * *